(12) United States Patent
Sugawara et al.

(10) Patent No.: US 8,809,496 B2
(45) Date of Patent: Aug. 19, 2014

(54) PRODUCTION METHOD OF 11-SUGAR SIALYLGLYCOPEPTIDE

(75) Inventors: Shuichi Sugawara, Fuji (JP); Kenji Osumi, Tokyo (JP)

(73) Assignee: The Noguchi Institute, Tokyo (JP)

( * ) Notice: Subject to any disclaimer, the term of this patent is extended or adjusted under 35 U.S.C. 154(b) by 169 days.

(21) Appl. No.: 13/394,197

(22) PCT Filed: Sep. 3, 2010

(86) PCT No.: PCT/JP2010/065165
§ 371 (c)(1),
(2), (4) Date: May 18, 2012

(87) PCT Pub. No.: WO2011/027868
PCT Pub. Date: Mar. 10, 2011

(65) Prior Publication Data
US 2012/0238723 A1    Sep. 20, 2012

(30) Foreign Application Priority Data

Sep. 3, 2009 (JP) ................................. 2009-203340
Jan. 13, 2010 (JP) ................................. 2010-005002

(51) Int. Cl.
| | | |
|---|---|---|
| C07K 9/00 | (2006.01) | |
| C07K 1/30 | (2006.01) | |
| C07K 1/16 | (2006.01) | |

(52) U.S. Cl.
USPC .......................................... 530/322; 530/329

(58) Field of Classification Search
USPC .................................................. 530/322, 329
See application file for complete search history.

(56) References Cited

U.S. PATENT DOCUMENTS

| | | |
|---|---|---|
| 5,834,423 A | 11/1998 | Koketsu et al. |
| 2002/0137068 A1 | 9/2002 | Haugland et al. |
| 2003/0211077 A1 | 11/2003 | An et al. |
| 2004/0181054 A1 | 9/2004 | Kajihara et al. |
| 2006/0205039 A1 | 9/2006 | Fukae |
| 2006/0228784 A1 | 10/2006 | Kajihara et al. |
| 2006/0270830 A1 | 11/2006 | Hreczuk-Hirst et al. |
| 2007/0282096 A1 | 12/2007 | Jain et al. |
| 2011/0129938 A1 | 6/2011 | Kobayashi et al. |

FOREIGN PATENT DOCUMENTS

| | | |
|---|---|---|
| JP | 8-99988 | 4/1996 |
| JP | 11-60599 | 3/1999 |
| JP | 2002-029974 | 1/2002 |
| JP | 2002-272479 | 9/2002 |
| JP | 2003-128703 | 5/2003 |
| JP | 2004-018841 | 1/2004 |
| JP | 2004-502703 | 1/2004 |
| JP | 2004-510767 | 4/2004 |
| JP | 2004-317398 | 11/2004 |
| JP | 2007-501888 | 2/2007 |
| WO | 96/02255 | 2/1996 |
| WO | 2004/058984 | 7/2004 |
| WO | 2004/070046 | 8/2004 |
| WO | 2004/092739 | 10/2004 |
| WO | 2010/010674 | 1/2010 |

OTHER PUBLICATIONS

Poetschke et al., "Morphology and electrical resistivity of melt mixed blends of polyethylene and carbon nanotube filled polycarbonate," Polymer, vol. 44, 2003, pp. 8061-8069.
English Translation of the International Preliminary Report on Patentability and Written Opinion for International Application No. PCT/JP2010/065165 dated Apr. 19, 2012.

*Primary Examiner* — Chih-Min Kam
(74) *Attorney, Agent, or Firm* — Greenblum & Bernstein, P.L.C.

(57) ABSTRACT

It is an object of the present invention to provide a method for producing an 11-sugar sialylglycopeptide easily and with good yield and a high degree of purity on an industrial scale from defatted bird egg yolks. The present invention provides a production method of an 11-sugar sialylglycopeptide. More specifically, the present invention provides a production method of an 11-sugar sialylglycopeptide comprising: an extraction step of extracting defatted bird egg yolks with water or a salt solution to obtain a liquid extract of a glycopeptide, a precipitation step of adding the liquid extract to a water-soluble organic solvent to precipitate the glycopeptide, and a desalting step of desalting the precipitate.

16 Claims, 9 Drawing Sheets

PRODUCTION METHOD OF 11-SUGAR SIALYLGLYCOPEPTIDE

SEQUENCE LISTING

The instant application contains a Sequence Listing which has been submitted in ASCII format via EFS-Web and is hereby incorporated by reference in its entirety. Said ASCII copy, created on Apr. 5, 2012, is named P41638.txt and is 745 bytes in size.

The present application is a U.S. national phase application of PCT/JP2010/065165, filed Sep. 3, 2010, which claims priority to JP Application No. 2010-005002 filed Jan. 13, 2010, and JP 2009-203340 filed Sep. 3, 2009.

TECHNICAL FIELD

The present invention relates to a production method of an 11-sugar sialylglycopeptide.

BACKGROUND ART

In recent years, attention has focused on sugar chains as biological molecules in addition to nucleic acids (DNA) and proteins.

It is understood that sugar chains present in membrane proteins and outside the cell participate in intercellular recognition and interaction. Moreover, it is understood that changes in intercellular recognition and interaction cause cancer, chronic disease, infection and aging.

For example, changes in sugar chain structure are known to occur in cancerous cells. Also, it is known that pathogenic viruses including influenza viruses infiltrate and infect cells by recognizing and binding to specific sugar chains.

It is understood that many sugar chains exist in the body in the form of glycoproteins and glycolipids and perform physiological functions by means of intercellular recognition and interaction and the like.

Sugar chains in the body not only have a variety of structures, but are present in tiny quantities and are often bound to proteins and the like, so generally, numerous steps are often required for purification thereof. The operations of sugar chain extraction and purification are known to be difficult.

With recent research advances in the field of sugar chemistry, research for enzymes which substitute human sugar chains for sugar chains of glycoproteins having yeast sugar chains has been accelerated, and human sugar chains can now be substituted for yeast sugar chains with high efficiency. It is possible that the cost to manufacture glycoproteins by such method becomes less expensive than that to manufacture glycoproteins having human sugar chains using animal cells.

For example, erythropoietin having a human sugar chain can be manufactured by substituting a human sugar chain for a yeast sugar chain of erythropoietin expressed in yeast.

According to such method, erythropoietin having a human sugar chain can be provided cheaply and in large quantities, with lower manufacturing costs than conventional methods using animal cells. Moreover, the sugar chain structures are uniform, ensuring the quality of a drug product. Thus, methods of supplying human sugar chains and substituting human sugar chains for the yeast sugar chains of glycoproteins expressed in yeast are considered extremely effective in the manufacture of antibody drugs and physiologically active proteins.

However, no method has yet been established for providing human sugar chains in large quantities, so there is demand for establishment of such methods.

In recent years, egg yolks have gained attention as a source of supply of human sugar chains. Egg yolks mainly contain complex-type biantennary N-glycans that are same as human sugar chains, thus human sugar chains could be supplied using egg yolks as the source if these sugar chains could be extracted efficiently and in large quantities.

For example, Patent Document 1 discloses preparing an 11-sugar sialylglycopeptide from defatted chicken egg yolks (powder).

Moreover, Non-patent Document 1 discloses obtaining a sugar chain peptide (SGP: sialylglycopeptide), which is extracted from the water-soluble fraction of chicken eggs. The SGP is a compound in which a peptide residue of a peptide chain consisting of 6 amino acid residues is bound to the reducing terminal of a complex-type glycan chains consisting of 11 sugar residues, which is human sugar chain.

Further, Patent Document 2 discloses a method of manufacturing a sialic acid-containing oligosaccharide by extraction with water or a salt solution from defatted bird egg yolks.

PRIOR ART

Patent Document

[Patent Document 1] WO 96/02255
[Patent Document 2] Patent Publication JPA-H8-99988

Non-Patent Document

[Non-patent Document 1] Akira Seko, Mamoru Koketsu, Masakazu Nishizono, Yuko Enoki, Hisham R. Ibrahim, Lekh Raj Juneja, Mujo Kim and Takehiko Yamamoto, Biochimica at Biophysica Acta, 1997, Vol. 1335, p. 23-32

SUMMARY OF THE INVENTION

Problems to be Solved by the Invention

However, the 11-sugar sialylglycopeptide prepared by the method disclosed in Patent Document 1 has a purity of 91%, so the method cannot really be considered as a method for isolating a pure sugar chain peptide (Manufacturing Example 13 of Patent Document 1). Moreover, the method disclosed in Patent Document 1 requires extraction with water from defatted chicken egg yolks (powder), concentration with a reverse osmosis membrane, and adsorption by an anionic exchange resin, followed by desalting, elution with an aqueous NaCl solution, concentration, and a further desalting process. Furthermore, in Patent Document 1 it is described that 5.6 g of a rnonosialylglycopeptide and 13.8 g of a disialylglycopeptide were obtained from 50 kg of defatted egg yolk, which is not a satisfactory yield.

Moreover, the method disclosed in Non-patent Document 1 is unsuited to large-volume processing since it involves purification by five kinds of column chromatography, and furthermore only about 8 mg of an 11-sugar sialylglycopeptide is obtained from one chicken egg.

Further, the method disclosed in Patent Document 2 is an industrial method of manufacturing a sialic acid-containing oligosaccharide using ultrafiltration, and in the method low-molecular-weight oligosaccharide chains, in which one or more sialic acid covalently binds to an oligosaccharide, containing no amino acids are released by enzymatic treatment.

It is an object of the present invention to provide a method for producing an 11-sugar sialylglycopeptide easily and with good yield and a high degree of purity on an industrial scale from defatted bird egg yolks.

Means for Solving the Problems

As a result of conducting intensive studies to solve these problems described above, the inventors of the present invention have found that by a production method comprising (1) a step of extracting a glycopeptide from defatted bird egg yolks, (2) a step of precipitating the glycopeptide in a water-soluble organic solvent, and (3) a desalting step, the above problems can be solved, thereby leading to completion of the present invention.

That is, the present invention is as follows.

[1] A production method of an 11-sugar sialylglycopeptide, comprising:
an extraction step of extracting defatted bird egg yolks with water or a salt solution to obtain a liquid extract of a glycopeptide,
a precipitation step of adding the liquid extract to a water-soluble organic solvent to precipitate the glycopeptide, and
a desalting step of desalting the precipitate.

[2] The production method according to [1], wherein the water-soluble organic solvent contains at least one selected from the group consisting of alcohol, ether, nitrile, ketone, amide and sulfoxide, having 1 to 5 carbon atoms.

[3] The production method according to [1], wherein the water-soluble organic solvent contains an alcohol having 1 to 5 carbon atoms.

[4] The production method according to [2] or [3], wherein the alcohol is selected from the group consisting of methanol, ethanol and 2-propanol.

[5] The production method according to any of [1] to [4], wherein the desalting step is a step in which the precipitate is retained on a resin and then washed with water.

[6] The production method according to [5], wherein the resin is a reverse-phase partition chromatography resin.

[7] The production method according to [6], wherein the reverse-phase partition chromatography resin is a chemically bonded silica gel resin.

[8] The production method according to [7], wherein the chemically bonded silica gel resin is a resin composed of silica chemically bonded with a group selected from the group consisting of dimethyloctadecyl, octadecyl, dimethyloctyl, octyl, butyl, ethyl, methyl, phenyl, cyanopropyl and aminopropyl groups.

[9] The production method according to any of [1] to [8], wherein the desalting step further comprises a step of eluting the 11-sugar sialylglycopeptide with an aqueous organic solvent.

[10] The production method according to [9], wherein the aqueous organic solvent contains at least one selected from the group consisting of acetonitrile, methanol and ethanol.

[11] The production method according to [9] or [10], wherein the concentration of the aqueous organic solvent is from 0.1 to 20% (v/v).

[12] A production method of an 11-sugar sialylglycopeptide, comprising:
an extraction step of extracting defatted bird egg yolks with water to obtain a liquid extract of a glycopeptide,
a precipitation step of adding the liquid extract to ethanol to precipitate the glycopeptide, and
a desalting step of desalting the precipitate with ODS resin.

[13] A production method of an 11-sugar sialylglycopeptide, comprising:
an extraction step of extracting defatted bird egg yolks with water to obtain a liquid extract of a glycopeptide,
a precipitation step of adding the liquid extract to ethanol to precipitate the glycopeptide, and
a step of retaining the precipitate on ODS resin, washing the precipitate on the ODS resin with water, and then eluting the glycopeptide with an aqueous organic solvent.

[14] The production method according to any of [1] to [13], wherein the 11-sugar sialylglycopeptide is a glycopeptide represented by the following Formula 1.

Formula 1:

[Chem. 1]

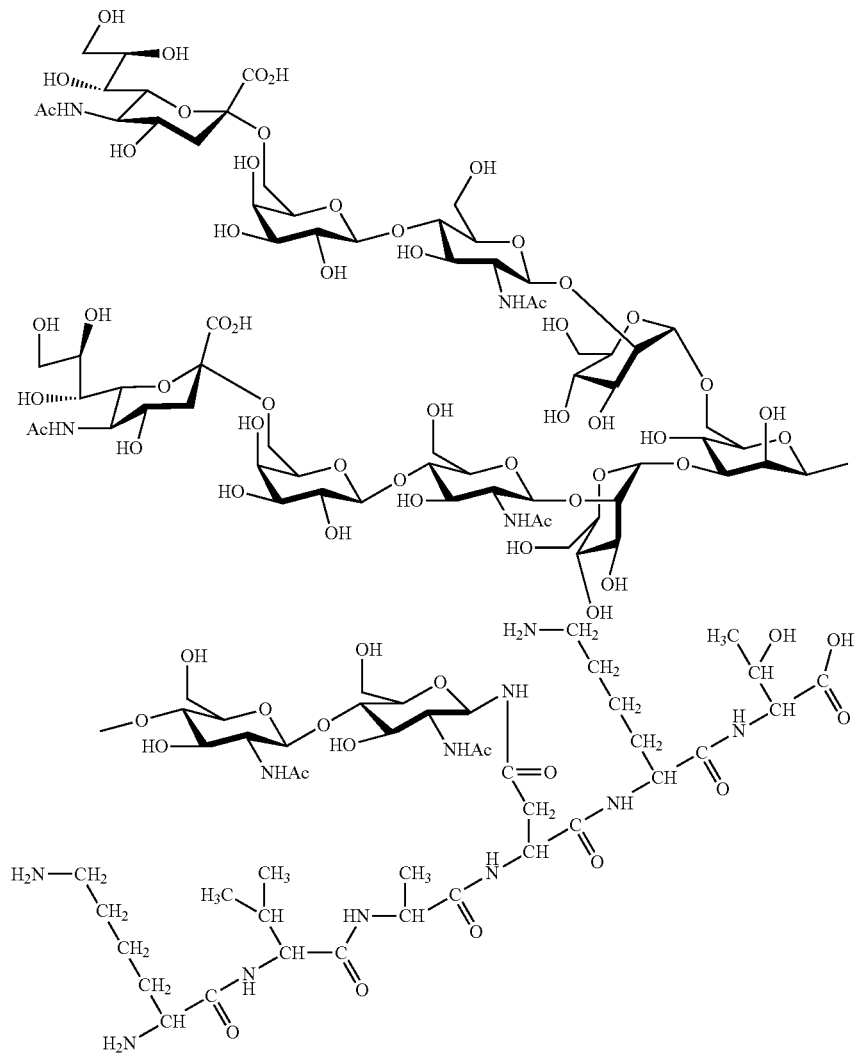

Advantageous Effect

According to the present invention, an 11-sugar sialylglycopeptide can be produced easily and with good yield and a high degree of purity on an industrial scale.

MODE FOR CARRYING OUT THE INVENTION

Figure 1:
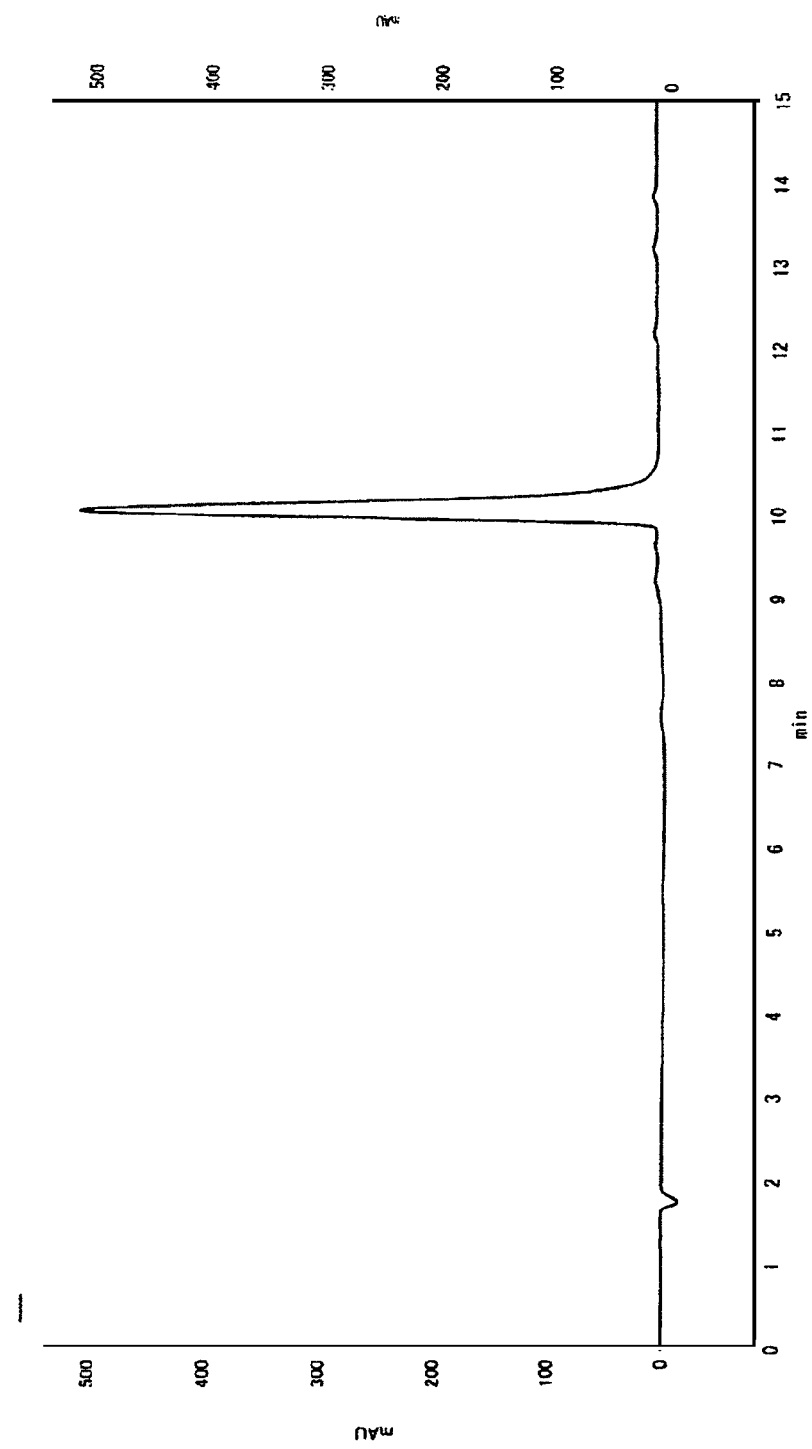
FIG. 1 shows a HPLC chart of an 11-sugar sialylglycopeptide manufactured in Example 1.

A mode for carrying out the invention (hereinafter referred to as "the present embodiment") is described below in detail. Note that the present invention is not intended to be limited to the following embodiment, and can be carried out in variety of ways within the scope of the gist of the invention.

The method production of an 11-sugar sialylglycopeptide (hereinafter sometimes referred to as "glycopeptide") of the present embodiment comprises an extraction step in which defatted bird egg yolks are extracted with water or a salt solution to obtain a liquid extract of a glycopeptide, a precipitation step in which the liquid extract is added to a water-soluble organic solvent to precipitate the glycopeptide, and a desalting step in which the precipitate is desalted.

In the present embodiment, the term "an 11-sugar sialylglycopeptide" refers to a glycopeptide in which a peptide chain consisting of 6 amino acid residues is bound to the reducing terminal of a complex sugar chain consisting of 11 sugar residues.

The 11 sugar residue part of the 11-sugar sialylglycopeptide is a sugar part having two sialyl groups at the non-reducing terminal.

An example of an 11-sugar sialylglycopeptide includes the glycopeptide represented by the following Formula 1.

Formula 1:

[Chem. 2]

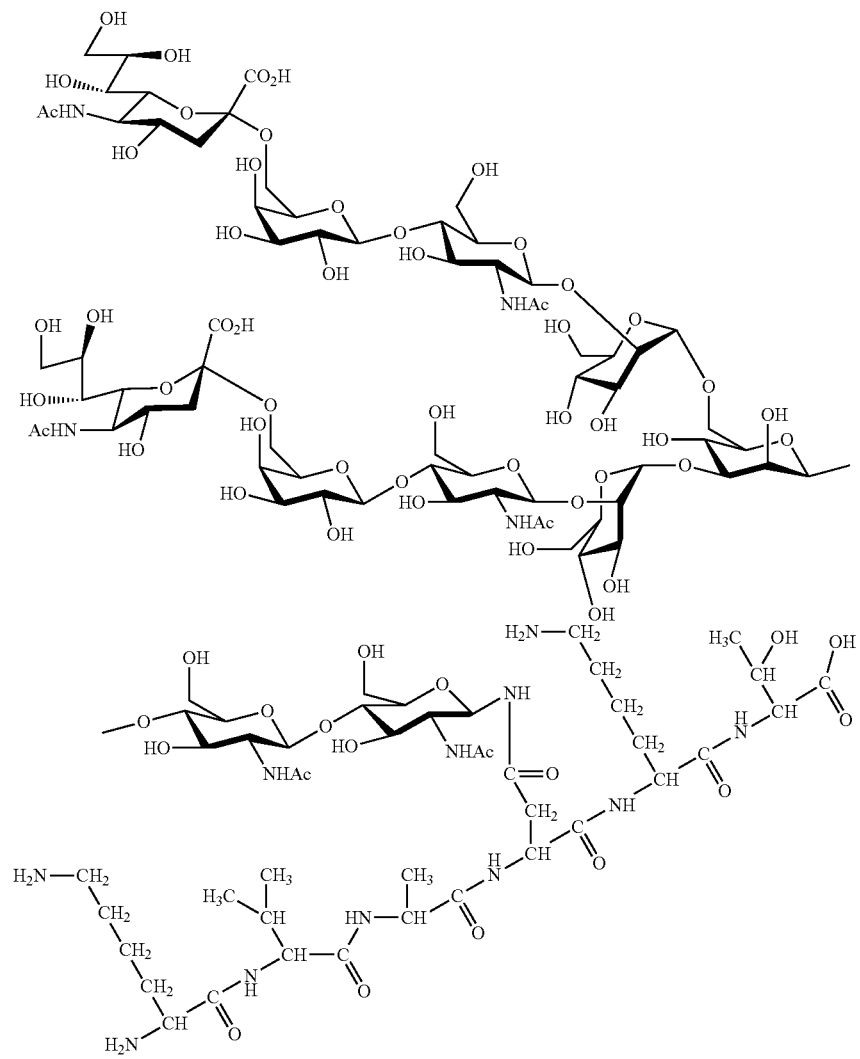

In the glycopeptide represented by the above Formula 1, the sugar chain part is bound to the Asn residue of Lys-Val-Ala-Asn-Lys-Thr (Seq. ID No. 1).

In the present embodiment, Lys, Val, Ala, Asn and Thr are 3-letter abbreviations for amino acids, representing lysine, valine, alanine, asparagine and threonine, respectively.

The amino acids may be L-amino acids or D-amino acids, and may be a mixture of L-amino and D-amino acids in any proportions, such as a racemic mixture. L-amino acids are preferred. Each amino acid may also be a derivative that is equivalent to that amino acid.

According to the production method of the present embodiment, an 11-sugar sialyiglycopeptide can be produced from defatted bird egg yolks on an industrial scale and easily, and preferably cheaply.

In a preferred mode of the present embodiment, an 11-sugar sialylglycopeptide can be produced with a high purity of 93% or more and with a high yield by a simple process on an industrial scale.

The extraction step in which defatted bird egg yolks are extracted with water or a salt solution to obtain a liquid extract of a glycopeptide is a step in which defatted bird egg yolks are suspended in water or a salt solution, and a mixture or the like of the glycopeptide is extracted to obtain a liquid extract which is a crude product of the glycopeptide.

Examples of the defatted bird egg yolks, but are not particularly limited to, include commercial defatted egg yolks and defatted egg yolks prepared from bird eggs.

Examples of the bird eggs, but are not particularly limited to, include the eggs of chickens, quail, geese, ducks, ostriches and pigeons. Chicken eggs are preferred because they contain large quantities of glycopeptides in the egg yolks.

The defatted bird egg yolks can be obtained by defatting treatment of whole bird eggs or egg yolks with an organic solvent.

The bird eggs may be in the form of raw bird eggs or dried egg powder obtained by drying, and chicken egg yolks, chicken egg yolk powder and the like are preferably used.

An example of the method of defatting treatment, but is not particularly limited to, includes a method to add an organic solvent to bird eggs and then separate the organic solvent layer by precipitation.

Examples of the organic solvent used in defatting treatment, but are not particularly limited to, include acetone, methanol, ethanol and 2-propanol. One kind of solvent can be used as the organic solvent, or a mixture of two or more solvents can be used.

The amount of the organic solvent added to the bird eggs in defatting treatment is not particularly limited, but defatting treatment can be performed using the organic solvent in the amount of from 1 to 5 times the amount of bird eggs by mass.

Defatting treatment, but is not particularly limited to, can be performed at the temperature of from 0 to 25° C.

The fat component in the bird eggs can be removed with the organic solvent by adding the organic solvent to the bird eggs and then agitating the organic solvent thoroughly with the bird eggs.

The method of separating the organic solvent from the precipitate is not particularly limited, but they can be centrifuged for from 5 to 30 minutes at from 2,000 to 10,000 rpm.

Defatting treatment using the organic solvent, but is not particularly limited to, is preferably performed from 2 to 6 times.

There are no particular limitations on the method of adding water or the salt solution to the defatted bird egg yolks to extract the glycopeptide from the defatted bird egg yolks. Examples of the salt solution used in the extraction process, but are not particularly limited to, include an aqueous sodium chloride solution and a phosphoric acid buffer. One kind of salt solution can be used, or a mixture of two or more kinds of salt solutions can be used.

The concentration of the salt solution, but is not particularly limited to, is from 0.0001 to 2.0% (w/v). The amount of water or the salt solution added to the defatted bird egg yolks is not particularly limited, but the glycopeptide can be extracted using water or the salt solution in the amount of from 0.1 to 50 times the amount of defatted bird egg yolks by mass.

Extraction of the glycopeptide, but is not particularly limited to, can be performed at the temperature of from 4 to 25° C.

The glycopeptide contained in the defatted bird egg yolks can be extracted with water or the salt solution by adding water or the salt solution to the defatted egg yolks and then agitating the defatted egg yolks thoroughly together with water or the salt solution.

The method of separating the defatted egg yolks from the extract containing the glycopeptide extracted with water or the salt solution is not particularly limited, but they may be centrifugation for from 5 to 30 minutes at from 2,000 to 10,000 rpm.

Extraction treatment using water or the salt solution, but is not particularly limited to, is preferably performed from 2 to 6 times or more preferably from 2 to 4 times.

Extraction is preferably performed using water.

The precipitation step of adding the liquid extract of the glycopeptide to a water-soluble organic solvent to precipitate the glycopeptide is a step in which by adding the liquid extract obtained in the extraction step, which contains the glycopeptide, to a water-soluble organic solvent, not only the liquid extract of the glycopeptides is concentrated, but also a more highly purified glycopeptides is obtained as a precipitate. In the precipitation step, a precipitate can also be obtained as a crude product by adding the water-soluble organic solvent to the liquid extract.

According to the present embodiment, the water-soluble organic solvent is not particularly limited as long as it includes an organic solvent compatible with water, but examples thereof include organic solvents having from 1 to 5 carbon atoms compatible with water.

The term "having from 1 to 5 carbon atoms" means that carbon atoms are from 1 to 5 in the solvent molecule.

Examples of such solvent, but are not particularly limited to, include solvents selected from the group consisting of alcohol such as methanol, ethanol, propanol, butanol, pentanol, ethylene glycol, glycerin and the like, ether such as diethyl ether, dioxane, dimethoxyethane, tetrahydrofuran and the like, nitrile such as acetonitrile and the like, ketone such as acetone and the like, amide such as dimethylformamide and the like, and sulfoxide such as dimethylsulfoxide and the like. One water-soluble organic solvent can be used, or a mixture of two or more solvents can be used.

The water-soluble organic solvent is preferably an alcohol having from 1 to 5 carbon atoms, and when the water-soluble organic solvent is an alcohol the precipitation step is a step of adding the liquid extract of the glycopeptide to the alcohol to precipitate the glycopeptide (hereinafter sometimes referred to as "alcohol precipitation step"), in which by adding the liquid extract containing the glycopeptide to the alcohol, not only the liquid extract of the glycopeptide is concentrated, but also a more highly purified glycopeptide is obtained as a precipitate.

Hereinafter, the precipitation step will be explained as an alcohol precipitation step, but a precipitation step using a water-soluble organic solvent other than alcohol (preferably a water-soluble organic solvent having from 1 to 5 carbon atoms) can be performed in the same way as the alcohol precipitation step. Reaction conditions such as the amount of the water-soluble organic solvent and the solvent temperature for precipitation, but are not particularly limited to, can be selected arbitrarily according to the solvent. The alcohol precipitation step will be described hereinafter. Reaction conditions such as the solvent amount and solvent temperature in the precipitation step can be set in the same way as in the alcohol precipitation step.

The amount of the alcohol used in the alcohol precipitation step is not particularly limited, but the glycopeptide can be extracted using the alcohol in the amount of from 2 to 20 times the amount of liquid extract by mass. The alcohol used in the alcohol precipitation step is preferably an alcohol having from 1 to 5 carbon atoms, more preferably an alcohol having from 1 to 3 carbon atoms. Specific examples of alcohol having 1 to 3 carbon atoms include methanol, ethanol and 2-propanol (isopropanol), and methanol and ethanol are preferred. Among them, ethanol is preferred. Ethanol is preferably used as the alcohol in the alcohol precipitation step when the glycopeptide is to be used for medical or pharmaceutical use.

According to the present embodiment, one kind of alcohol can be used as the alcohol in the alcohol precipitation step, or a mixture of two or more different alcohols can be used, or a mixture of an alcohol with another solvent can also be used.

When the alcohol solvent is a mixture, a mixed solvent, in which from 0.01 to 50% methanol or 2-propanol was added based on ethanol, can be used. A mixed solvent, in which from 0.01 to 50% acetone, acetonitrile or diethyl ether were added based on ethanol, can also be used.

The temperature for glycopeptide extraction, but is not particularly limited to, can be performed at the temperature of from 4 to 25° C.

The liquid extract of the glycopeptide obtained in the previous extraction step that is used in the alcohol precipitation step can be made into a clear liquid extract by filtering the liquid extract prior to the precipitation step. A concentrated liquid of the liquid extract, obtained by vacuum concentration or the like can be used.

The method of separating the glycopeptide in the alcohol precipitation step is not particularly limited, but they may be centrifuged for from 5 to 30 minutes at from 2,000 to 10,000 rpm, or separation may be performed by settling at from 4 to 25° C.

The more highly purified glycopeptide can be obtained by dissolving the resulting glycopeptide in water or the salt solution, and then repeating the alcohol precipitation step. Since the glycopeptide does not dissolve in alcohol, the alcohol precipitation step can be repeated as necessary to remove impurities. The more highly purified glycopeptide can be obtained by repeating the alcohol precipitation step, and precipitation of the glycopeptide, but is not particularly limited to, is preferably performed from 2 to 6 times, more preferably from 2 to 4 times.

The desalting step of desalting the precipitate of the glycopeptide is a step in which salts are removed from the precipitate, which is the crude product containing the glycopeptide obtained in the precipitation step.

Various known desalting methods, but are not particularly limited to, can be used in the desalting step. Desalting, but is not particularly limited to, can be performed using ion-exchange resin, an ion-exchange membrane, gel filtration, a dialysis membrane, an ultrafiltration membrane or a reverse osmosis membrane in the desalting step. In the desalting step, the precipitate obtained in the precipitation step can be retained on a resin and then desalted by being washed with water for example.

According to the present embodiment, an 11-sugar sialyl-saccharide can be easily manufactured on an industrial scale by desalting the precipitate obtained by means of the aforementioned extraction and precipitation steps.

A conventional method such as that described in Patent Document 1, requires extraction with water from defatted chicken egg yolk (powder), concentration with a reverse osmosis membrane, and adsorption by an anionic exchange resin, followed by desalting, elution with an aqueous NaCl solution, concentration, and a further desalting process, so this is not a method that can be easily applied on an industrial scale.

The precipitate can be retained on a resin by a method using a known form of binding such as adsorption, supporting or the like. The precipitate can be retained on the resin to a degree that the precipitate is not washed away with the wash liquid during water washing.

An example of the resin, but is not particularly limited to, includes a reverse-phase partition chromatography resin. A reverse-phase chromatography resin refers to a resin such as a silica gel or polymer resin Examples thereof, but are not particularly limited to, include poly(styrene/divinylbenzene) polymer gel resin, polystyrene-divinylbenzene resin, polyhydroxymethacrylate resin, styrene-vinyl benzene copolymer resin, polyvinyl alcohol resin, polystyrene resin, polymethacrylate resin, chemically bonded silica gel resin.

An example of the chemically bonded silica gel resin, but is not particularly limited to, includes resin obtained by reacting a silane coupling agent such as dimethyloctadecyl chlorosilane with a porous silica gel. Also, examples thereof include resins obtained by using different silylation agents to chemically bind groups selected from the group consisting of dimethyloctadecyl, octadecyl (C18), trimethyloctadecyl, dimethyloctyl, octyl (C8), butyl, ethyl, methyl, phenyl, cyanopropyl and aminopropyl groups to a silica gel by the same methods. Alternatively, resins obtained by binding a $C_{22}$ docosyl (C20) group and a $C_{30}$ triacontyl (C30) group may be used.

In the present embodiment, a preferred chemically bonded silica gel resin is an octadecyl silica gel resin (ODS resin) comprising octadecyl groups supported on a silica gel substrate.

The desalting step preferably comprises a step of eluting the glycopeptide (11-sugar sialylglycopeptide) retained on the resin after desalting, by using an aqueous organic solvent and the purity of the 11-sugar sialylglycopeptide can be improved by means of the eluting step in which the glycopeptide is eluted with the aqueous organic solvent after being desalted in the desalting step. In a more preferred mode, the purity of the 11-sugar sialylglycopeptide can be 93% or more. For example, the purity of the glycopeptide can be improved still further by repeating the desalting step (eluting step). Increasing the purity of the glycopeptide is desirable for example because it reduces interference reactions from impurities and increases the reaction efficiency of the transfer reaction when the sugar chain part of the glycopeptide obtained by the present embodiment is transferred to another sugar chain or sugar chain derivative (including in the case of being transferred to a sugar chain of a glycopeptide) by means of a transfer reaction using a glycosyltransferase such as Endo-M.

The organic solvent used in the elution step contains, for example, at least one selected from the group consisting of acetonitrile, methanol and ethanol, and the concentration of the organic solvent is preferably from 0.1 to 20% (v/v) as the concentration of the organic solvent in the aqueous solution.

The desalting step or the eluting step, but is not particularly limited to, can be performed at the temperature of from 4 to 25° C.

In addition to the desalting step by using resin, desalting from the precipitate obtained in the precipitation step can also be performed by using a separation membrane as the desalting step.

In such desalting step, desalting the precipitate can be performed by using, for example, an ultrafiltration membrane or a reverse osmosis membrane.

Examples of the membrane used in the desalting step, but are not particularly limited to, include flat membranes, hollow fiber membranes, spiral membranes, tubular membranes having polyacrylonitrile, polysulfone, polyether sulfone, polyvinylidene fluoride, polytetrafluoroethylene, aromatic polyamide, cellulose acetate and polyvinyl alcohol as base materials. Further desalting can be also performed by using an ion-exchange resin, ion-exchange membrane, gel filter, dialysis membrane, ultrafiltration membrane or reverse osmosis membrane as such membrane.

A known method of purifying peptides, sugars, glycopeptides and the like can be used as the method of purifying the glycopeptide in the present embodiment, and examples thereof, but are not particularly limited, include normal-phase chromatography, reverse-phase chromatography, ion-exchange chromatography, affinity chromatography, and size exclusion chromatography. Examples of the carrier used in reverse-phase chromatography, but is not particularly limited, include carriers octadecyl, octyl, phenyl, cyanopropyl, methyl or the like fixed on a filler surface with silica as the base material, and among them examples include ODS resins.

A purification method by column chromatography by using the silica gel resin filler such as ODS resin may comprise a step of desalting the salts contained in the glycopeptide obtained by precipitation, and may also comprise a step of eluting the glycopeptide with an aqueous organic solvent.

The glycopeptide can be desalted by washing the silica gel resin with the glycopeptide added thereto and retained thereon, by using water in the amount of from 1 to 50 times the mass of the silica gel resin.

After desalting, the glycopeptide can be obtained by elution with an aqueous organic solvent. In a more preferred mode, the purity of the 11-sugar sialylglycopeptide can be 93% or more.

The glycopeptide can be obtained by elution from the resin by using the aqueous organic solvent in the amount of from 1 to 50 times the mass of the resin, in the silica gel resin such as the ODS resin with the glycopeptide added thereto and retained thereon.

Examples of the aqueous organic solvent, but are not particularly limited to, include an aqueous solution of at least one organic solvent selected from the group consisting of acetonitrile, methanol and ethanol.

Acetonitrile is preferred for the aqueous organic solvent, and by performing the elution step with an aqueous acetonitrile solution in particular, it is possible to dramatically increase the purity of separation in the elution step by separating the desired glycopeptide from a particular impurity (a glycopeptide with partially cleaved terminal sialic acid) to thereby obtain the glycopeptide with a purity of 93% or more.

The concentration of the aqueous organic solvent is preferably from 0.1 to 20% (v/v), more preferably from 0.5 to 20% (v/v), further preferably 10% or less (v/v), further more preferably 5% or less (v/v). The concentration of the aqueous organic solvent is preferably from 0.5 to 3% (v/v).

In a conventional method such as that described in Patent Document 1, the operation of elution from the resin requires resin adsorption by using an anionic exchange resin for example, followed by an elution operation by using a salt solution or an acidic solution. However, elution by using the acidic solution is undesirable because it is considered that there is the risk of dissociating the terminal sialic acid from the glycopeptide. In the case of elution by using the salt solution, further desalting from the eluate is required, increasing the number of steps in large-scale manufacturing. The present embodiment is suited to large-scale manufacturing because elution is preferably performed with the aqueous organic solvent in the elution step, eliminating the need for desalting of the eluate and reducing the number of steps. The method of the present embodiment is also advantageous because the pH is not changed during concentration of the eluate, and there is less breakdown of the sugar chain part of the glycopeptide than in conventional methods.

In the step of eluting the glycopeptide with the aqueous organic solvent, elution can be performed gradually from water with a gradient into the aqueous organic solvent as the eluate.

The eluted glycopeptide can be obtained in powder form by vacuum concentration and drying and the like of the aqueous organic solvent.

In the present embodiment, the resulting glycopeptide can also be further purified in another alcohol precipitation step. The glycopeptide can also be adsorbed again on a silica resin such as an ODS resin, and eluted again from the resin with an aqueous organic solvent in the amount of from 1 to 50 times the amount of resin to provide a glycopeptide with a higher degree of purity (98% or more).

EXAMPLE

The present embodiment is more specifically described below based on examples and comparative examples, but the present embodiment is not intended to be limited only to these examples. The measurement methods used in the present embodiment are as follows.

[HPLC Analysis]

HPLC analysis was performed under the following measurement conditions using a GL Sciences HPLC GL-7400 System with a Cadenza CD-C18 column (Imtakt, 150×2 mm).

Measurement Conditions:
Gradient: 2%→17% (15 min), $CH_3CN$ in 0.1% TFA solution
Flow rate: 0.3 mL/min
UV: 214 nm

[$^1$H-NMR Measurement]

2 mg of sample was dissolved in 0.4 mL of $D_2O$, and the $^1$H-NMR spectrum was measured with a JEOL JNM-600 (600 MHz).

[LC/MS Measurement]

LC/MS measurement was performed under the following measurement conditions. The following LC and MS systems were used.

LC: Agilent 1100 Series
Column: Cadenza CD-C18 (Imtakt, 150×2 mm)
Column temperature: 40° C.
Flow rate: 0.2 mL/min
UV: 262 nm
Gradient: 40%→100% (30 min), $CH_3CN$ in 0.05% formic acid solution
MS: Thermo Electron Corp. LCQ
Ionization: ESI
Mode: Positive Example 1

350 mL of ethanol was added to 10 chicken egg yolks, and thoroughly agitated. The resulting mixture was centrifuged for 20 minutes at 8,000 rpm, and the supernatant was removed by decantation to obtain a precipitate. The operations of adding 300 mL of ethanol to the resulting precipitate, thoroughly agitating, and then centrifuging and removing the supernatant were repeated 3 times to obtain 150 g of defatted egg yolks as a precipitate.

200 mL of water was added to 150 g of the resulting defatted egg yolks described above, and thoroughly agitated. The resulting mixture was centrifuged for 20 minutes at 8,000 rpm, and a supernatant was obtained by decantation. The operations of adding 100 mL of water to the precipitate obtained by decantation, thoroughly agitating, and then centrifuging and collecting the supernatant were repeated 3 times. The collected supernatant was filtered with a glass filter and vacuum concentrated to 100 mL. The resulting concentrated solution was poured into 700 mL of ethanol, the resulting precipitate was centrifuged for 20 minutes at 8,000 rpm, and collected by removing the supernatant by decantation. The resulting precipitate was dissolved in water, and then poured into ethanol again. These operations were repeated 3 times. The resulting precipitate was collected to obtain 1.58 g of a crude glycopeptide.

Using 25 g of Wakogel (100C18) silica gel resin as the ODS resin, the resin was washed with methanol, and substituted with water. 1.5 g of the crude glycopeptide dissolved in 5 mL of water was added to the water-substituted resin. The resin with the crude glycopeptide added thereto was washed with 100 mL of water, and the glycopeptide was eluted with 2% aqueous acetonitrile solution. The eluate was freeze-dried to obtain 117 mg of a glycopeptide.

Figure 2:
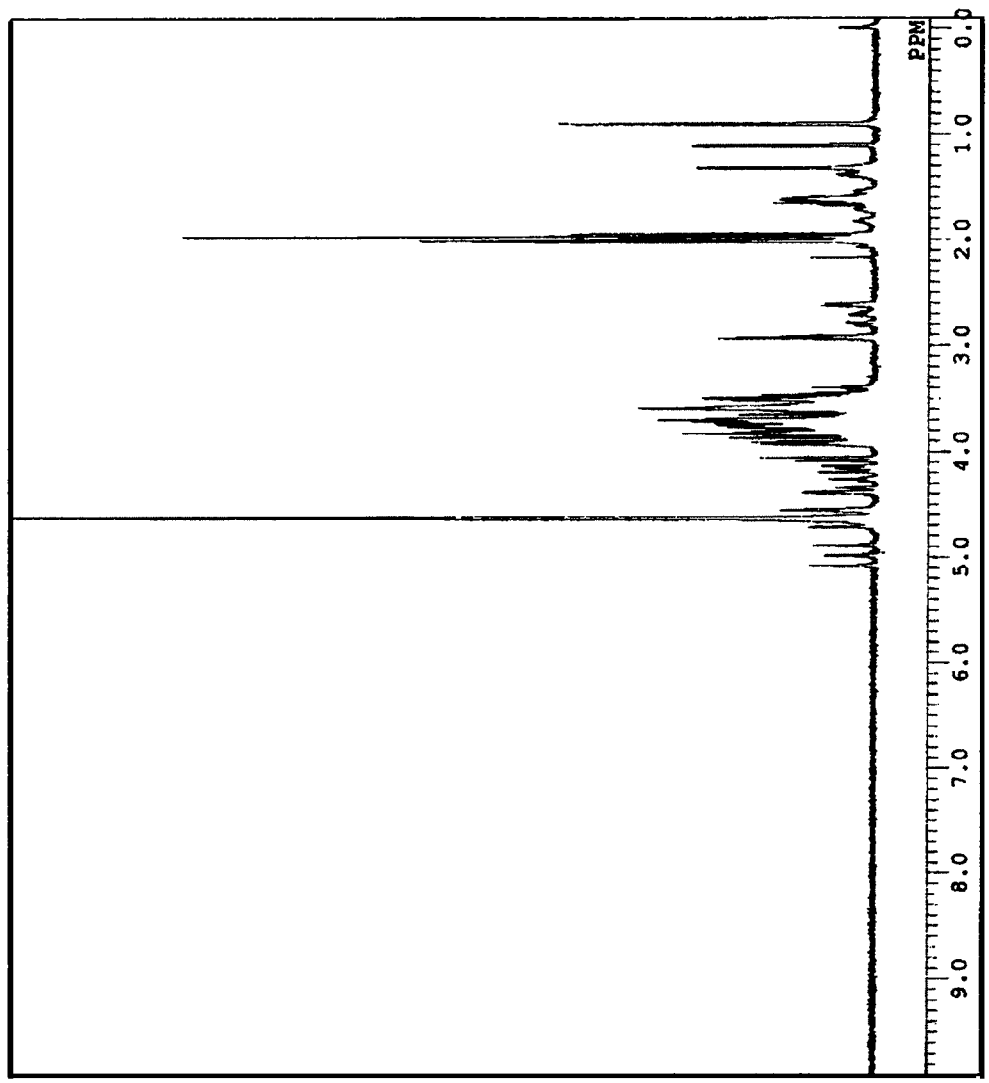
FIG. 2 shows a $^1$H-NMR chart of an 11-sugar sialylglycopeptide manufactured in Example 1.

The results of HPLC and $^1$H-NMR measurement of the resulting glycopeptide are shown in FIGS. 1 and 2. The purity was 95% according to HPLC. The resulting glycopeptide was shown by comparison with a standard product (manufactured by Tokyo Chemical Industry Co.), to have the structure represented by Formula 1 described above.

10 mg of the resulting glycopeptide was reacted with Fmoc-OSu (N-(9-fluorenylmethoxycarbonyloxy) succinimide (manufactured by Peptide Institute, Inc.) in 1.5 mL of 1M sodium hydrogen carbonate-acetone (volume ratio 2/3) solvent to obtain 10 mg of a reaction product with introduced Fmoc groups. The reaction product was subjected to LC/MS measurement. Production of a compound with an estimated molecular weight of 3530.6 having 3 Fmoc groups introduced into 3 amino groups of the glycopeptide was confirmed, showing that this was the glycopeptide of Formula 1 described above.

Figure 3:
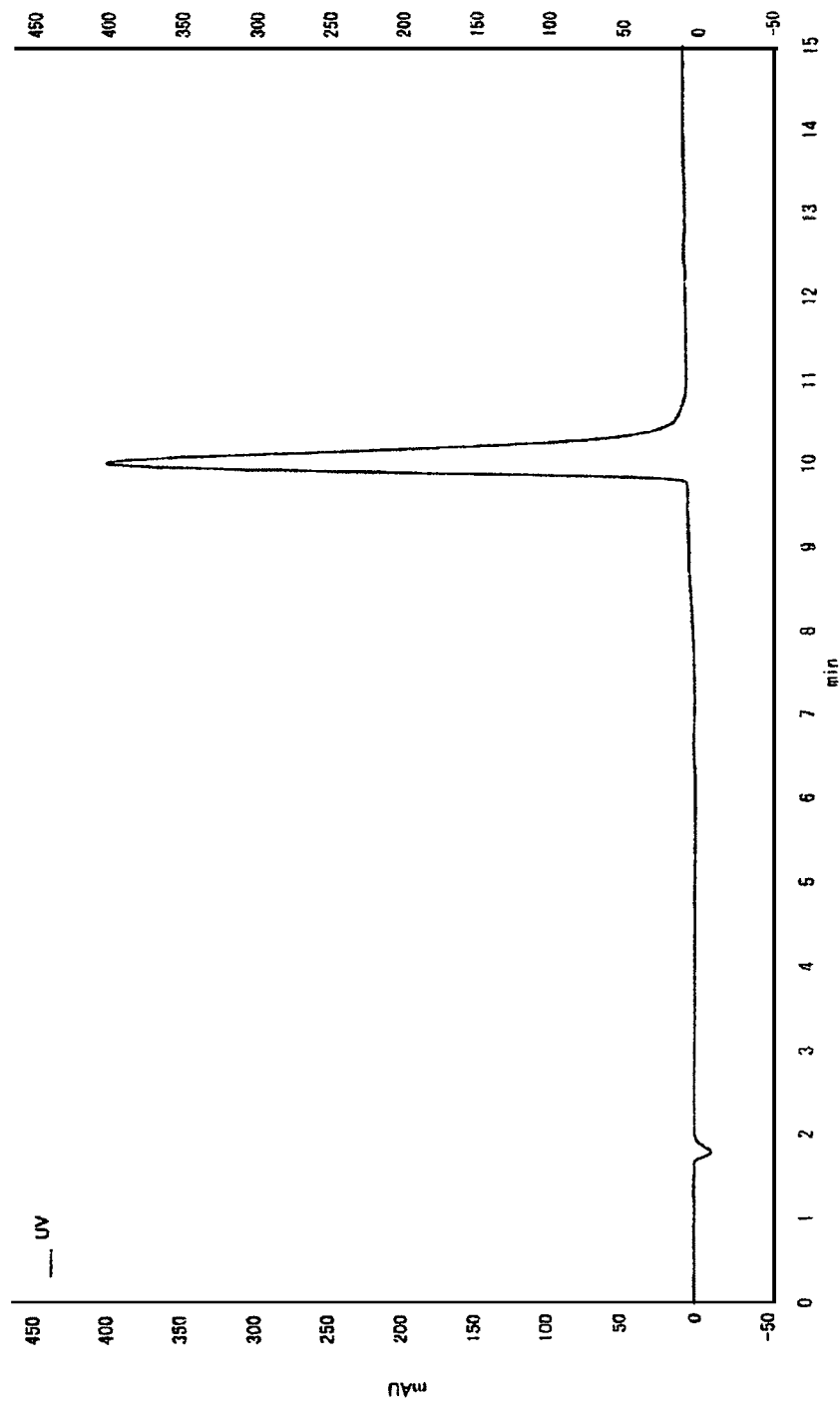
FIG. 3 shows a HPLC chart of an 11-sugar sialylglycopeptide manufactured in Example 1 with further elution using ODS resin.

A glass column was then packed with 25 g of Wakogel (100C18) silica gel resin as an ODS resin, and the resin was washed with methanol and then substituted with water. 50 mg of the glycopeptide obtained above was dissolved in 1 mL of water, and added to the water-substituted resin. The resin with the added glycopeptide was washed with 100 mL of water, and the glycopeptide was eluted again with 2% aqueous acetonitrile solution. The eluate was freeze-dried to obtain 30 mg of glycopeptide. The result of HPLC measurement of the resulting glycopeptide is shown in FIG. 3. The purity was 99% according to HPLC.

Example 2

1.1 L of acetone was added to 50 chicken egg yolks, and thoroughly agitated. The resulting mixture was centrifuged for 15 minutes at 8,000 rpm, and the supernatant was removed by decantation to obtain a precipitate. The operations of adding 700 mL of ethanol to the resulting precipitate, thoroughly agitating, and then centrifuging and removing the supernatant were repeated twice to obtain 500 g of defatted egg yolks as a precipitate.

600 mL of water was added to 500 g of the resulting defatted egg yolks described above, and thoroughly agitated. The resulting mixture was centrifuged for 15 minutes at 8,000 rpm, and the supernatant was obtained by decantation. The operations of adding 400 mL of water to the precipitate obtained by decantation, thoroughly agitating, and then centrifuging and collecting the supernatant were repeated 3 times. The collected supernatant was filtered with a glass filter and vacuum concentrated to 400 mL. The resulting concentrated solution was poured into 2 L of ethanol, the resulting precipitate was centrifuged for 15 minutes at 8,000 rpm, and collected by removing the supernatant by decantation. The resulting precipitate was dissolved in water, and poured into ethanol. These operations were repeated 3 times. The resulting precipitate was collected to obtain 9.0 g of a crude glycopeptide.

A glass column was packed with 50 g of Wakogel (100C18) silica gel resin as an ODS resin, and the resin was washed with methanol and then substituted with water. 9.0 g of the crude glycopeptide was dissolved in 80 mL of water, and added to the water-substituted resin. The resin with the added crude glycopeptide was washed with 200 mL of water, and the glycopeptide was eluted with 2% aqueous acetonitrile solution. The eluate was freeze-dried to obtain 389 mg of a glycopeptide.

Figure 4:
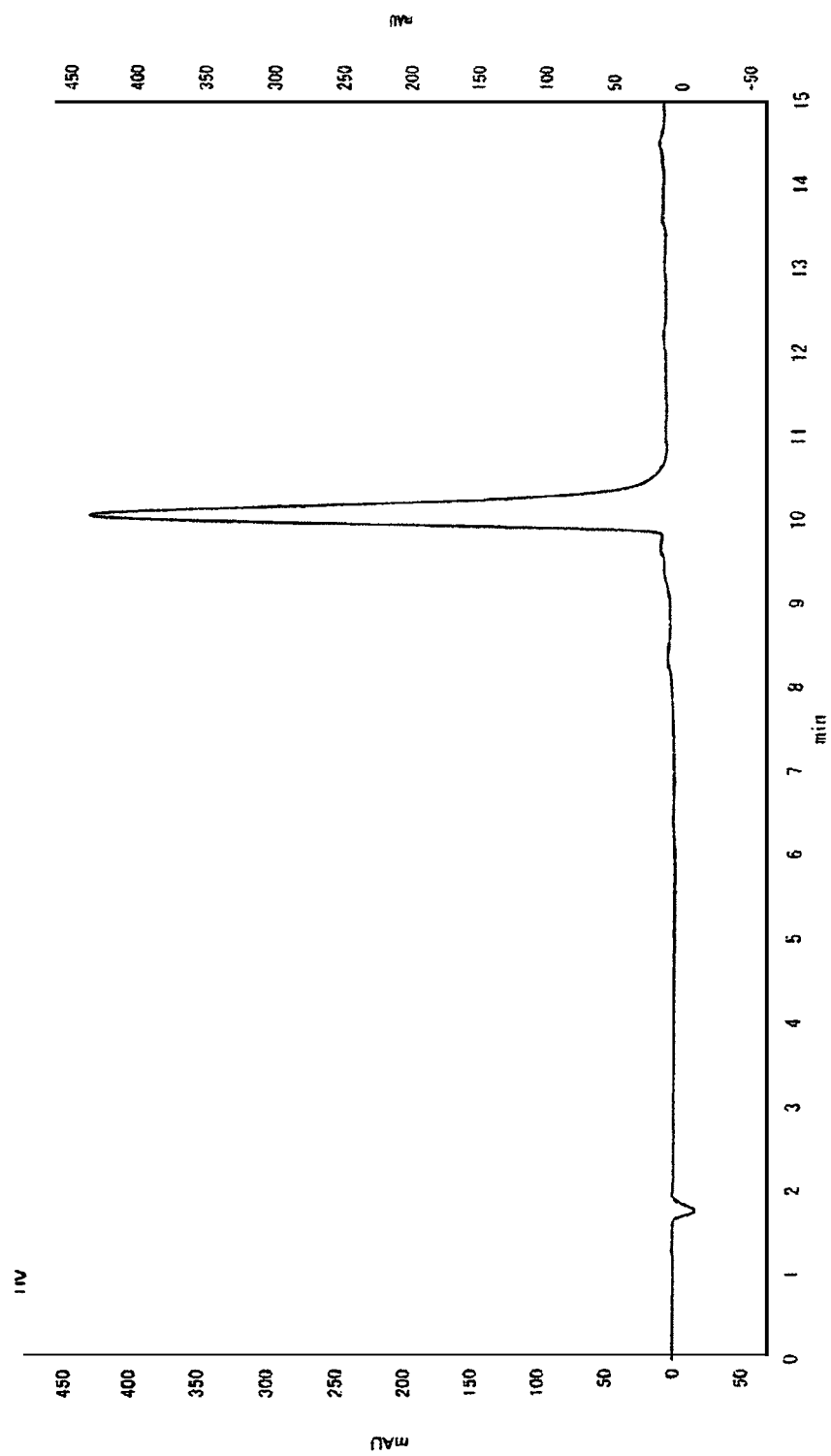
FIG. 4 shows a HPLC chart of an 11-sugar sialylglycopeptide manufactured in Example 2.

The result of HPLC measurement of the resulting glycopeptide is shown in FIG. 4. The purity was 96% according to HPLC. The resulting glycopeptide was shown by comparison with a standard product (manufactured by Tokyo Chemical Industry Co.), to have the structure represented by Formula 1 described above.

Example 3

100 mL of acetone was added to 30 g of chicken egg yolk powder (manufactured by Kewpie Egg Corp.) and thoroughly agitated, and the supernatant was removed by decantation. The operations of adding a further 50 mL of acetone, thoroughly agitating and removing the supernatant by decantation were repeated twice.

After acetone washing, 50 mL of ethanol was added and thoroughly agitated. The resulting mixture was centrifuged for 20 minutes at 8,000 rpm, and the supernatant was removed by decantation to obtain a precipitate. 50 mL of ethanol was added to the resulting precipitate and thoroughly agitated, followed by centrifugation, and the supernatant was removed to obtain 40 g of defatted egg yolks as a precipitate.

200 mL of water was added to 40 g of the resulting defatted egg yolks described above, and thoroughly agitated. The resulting mixture was centrifuged for 20 minutes at 8,000 rpm, and a supernatant was obtained by decantation. The operations of adding 100 mL of water to the precipitate obtained by decantation, thoroughly agitating, and then centrifuging and collecting the supernatant were repeated 3 times. The collected supernatant was filtered with a glass filter and vacuum concentrated to 50 mL. The resulting concentrated solution was poured into 300 mL of ethanol, the resulting precipitate was centrifuged, and collected by removing the supernatant by decantation. The resulting precipitate was dissolved in water, then poured into ethanol again, and centrifuged to obtain 297 mg of a crude glycopeptide.

Using 25 g of Wakogel (100C18) silica gel resin as the ODS resin, the resin was washed in methanol, and substituted with water. 297 mg of the crude glycopeptide dissolved in 2 mL of water was added to the water-substituted resin. The resin with the crude glycopeptide added thereto was washed with 100 mL of water, and the glycopeptide was eluted with 2% aqueous acetonitrile solution. The eluate was freeze-dried to obtain 10 mg of a glycopeptide.

The resulting glycopeptide was shown by comparison with a standard product (manufactured by Tokyo Chemical Industry) to have the structure represented by Formula 1 described above.

Example 4

800 mL of methanol was added to 30 chicken egg yolks, and thoroughly agitated. The resulting mixture was centrifuged for 20 minutes at 8,000 rpm, and the supernatant was removed by decantation to obtain a precipitate. The operations of adding 600 mL of methanol to the resulting precipitate, thoroughly agitating, and then centrifuging and removing the supernatant were repeated 3 times to obtain 450 g of defatted egg yolk as a precipitate.

500 mL of water was added to 450 g of the resulting defatted egg yolk described above, and thoroughly agitated. The resulting mixture was centrifuged for 20 minutes at 8,000 rpm, and a supernatant was obtained by decantation. The operations of adding 500 mL of water to the precipitate obtained by decantation, thoroughly agitating, and then centrifuging and collecting the supernatant were repeated 3 times. The collected supernatant was filtered with a glass filter and vacuum concentrated to 300 mL. The resulting concentrated solution was poured into 2 L of denatured alcohol (methanol-denatured ethanol, ethanol containing 1% methanol), the resulting precipitate was centrifuged for 20 minutes at 8,000 rpm and collected by removing the supernatant by decantation. The resulting precipitate was dissolved in water, and then poured again into methanol-denatured ethanol. These operations were repeated 3 times. The resulting precipitate was collected to obtain 4.5 g of a crude glycopeptide.

Using 50 g of Wakogel (100C18) silica gel resin as the ODS resin, the resin was washed with methanol and substituted with water. 4.5 g of the crude glycopeptide dissolved in 20 mL of water was added to the water-substituted resin. The resin with the crude glycopeptide added thereto was washed with 100 mL of water, and the glycopeptide was eluted with 2% aqueous acetonitrile solution. The eluate was freeze-dried to obtain 285 mg of a glycopeptide.

Figure 5:
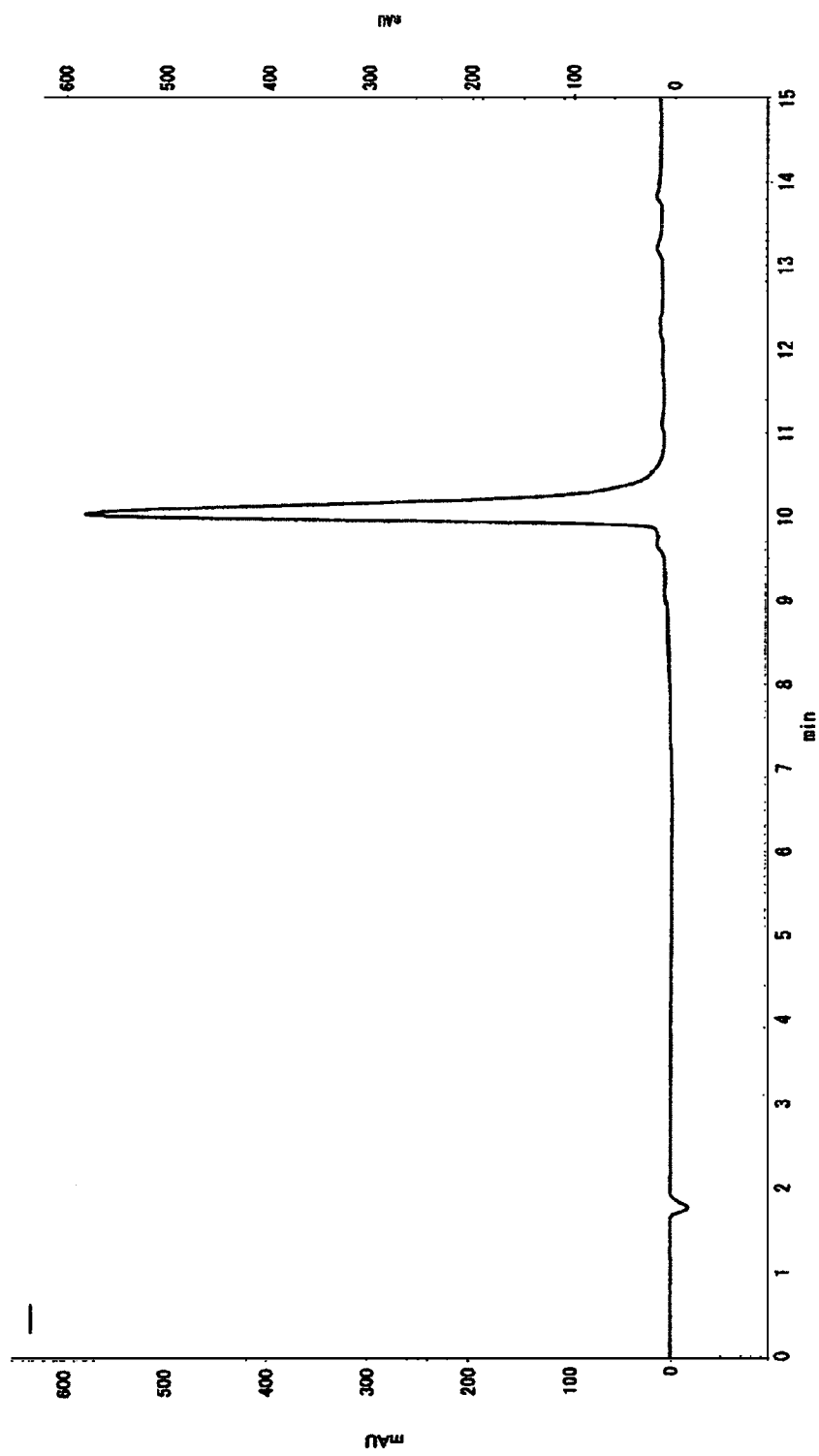
FIG. 5 shows a HPLC chart of an 11-sugar sialylglycopeptide manufactured in Example 4.

The result of HPLC measurement of the resulting glycopeptide is shown in FIG. 5. The purity was 93% according to HPLC. The resulting glycopeptide was shown by comparison with a standard product (manufactured by Tokyo Chemical Industry) to have the structure represented by Formula 1 described above.

Example 5

550 mL of isopropanol was added to 20 chicken egg yolks, and thoroughly agitated. The resulting mixture was centrifuged for 20 minutes at 8,000 rpm, and the supernatant was removed by decantation to obtain a precipitate. The operations of adding 300 mL of isopropanol to the resulting precipitate, thoroughly agitating, and then centrifuging and removing the supernatant were repeated 3 times to obtain 300 g of defatted egg yolks as a precipitate.

300 mL of water was added to 300 g of the resulting defatted egg yolks described above, and thoroughly agitated. The resulting mixture was centrifuged for 20 minutes at 8,000 rpm, and a supernatant was obtained by decantation. The operations of adding 300 mL of water to the precipitate obtained by decantation, thoroughly agitating, and then centrifuging and collecting the supernatant were repeated 3 times. The collected supernatant was filtered with a glass filter and vacuum concentrated to 700 mL. The resulting concentrated solution was poured into 3 L of denatured alcohol (methanol-denatured ethanol, ethanol containing 1% methanol), and the resulting precipitate was centrifuged for 20 minutes at 8,000 rpm and collected by removing the supernatant by decantation. The resulting precipitate was dissolved in water, and poured into a mixture of methanol and ethanol (methanol:ethanol=3:7, volume ratio). These operations were repeated 3 times. The resulting precipitate was collected to obtain 3.3 g of a crude glycopeptide.

Using 50 g of Wakogel (100C18) silica gel resin as the ODS resin, this resin was washed with methanol and substituted with water. 3.3 g of the crude glycopeptide dissolved in 20 mL of water was added to the water-substituted resin. The resin with the crude glycopeptide added thereto was washed with 100 mL of water, and the glycopeptide was eluted with 2% aqueous acetonitrile solution. The eluate was freeze-dried to obtain 186 mg of a glycopeptide.

Figure 6:
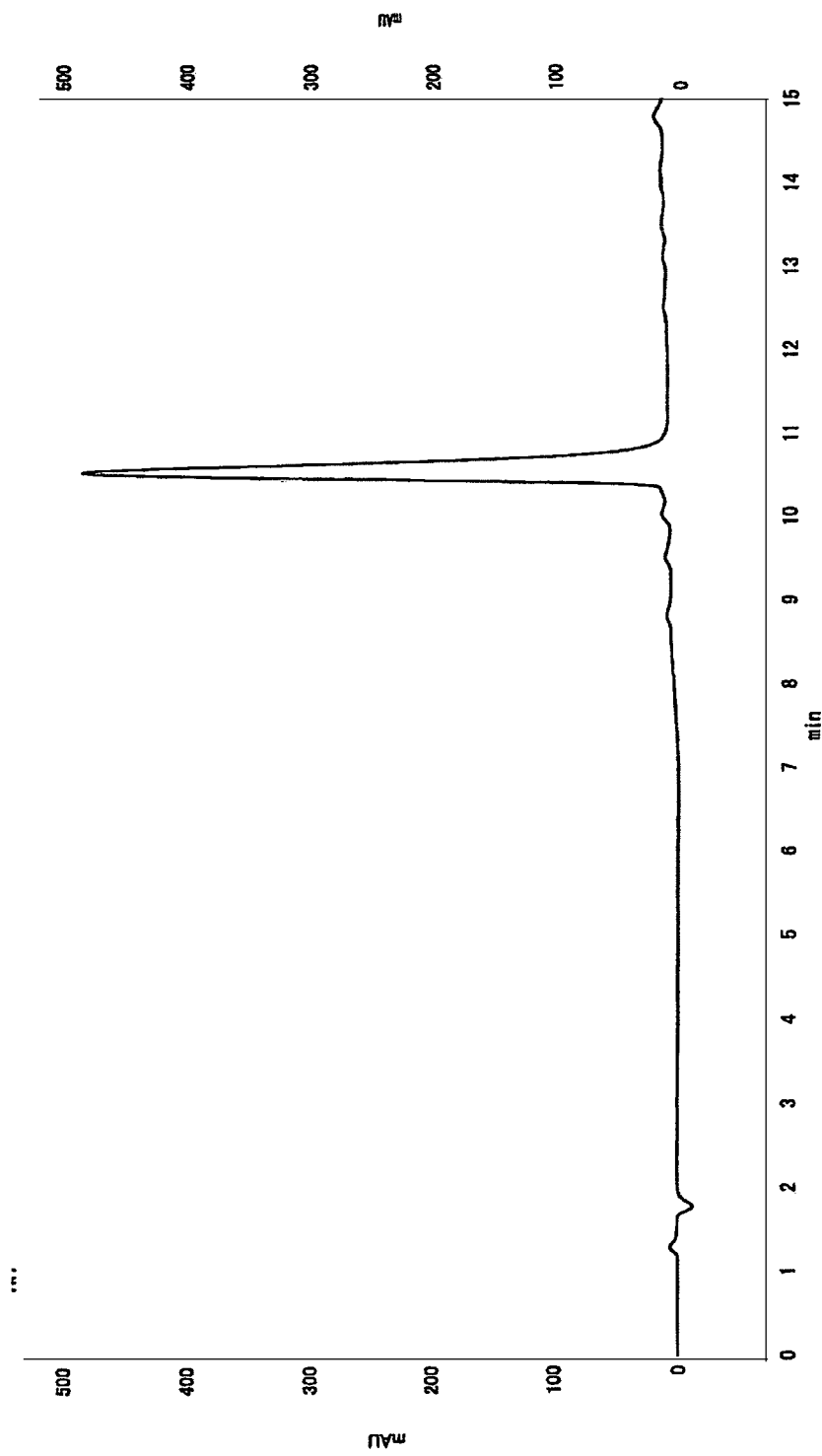
FIG. 6 shows a HPLC chart of an 11-sugar sialylglycopeptide manufactured in Example 5.

The results of HPLC measurement of the resulting glycopeptide is shown in FIG. 6. The purity was 94% according to HPLC. The resulting glycopeptide was shown by comparison with a standard product (manufactured by Tokyo Chemical Industry) to have the structure represented by Formula 1 described above.

Example 6

500 mL of acetone was added to 20 chicken egg yolks, and thoroughly agitated. The resulting mixture was centrifuged for 20 minutes at 8,000 rpm, and the supernatant was removed by decantation to obtain a precipitate. The operations of adding 300 mL of acetone to the resulting precipitate, thoroughly agitating, and then centrifuging and removing the supernatant were repeated 3 times to obtain 300 g of defatted egg yolks as a precipitate.

300 mL of water was added to 300 g of the resulting defatted egg yolks described above, and thoroughly agitated. The resulting mixture was centrifuged for 20 minutes at 8,000 rpm, and a supernatant was obtained by decantation. The operations of adding 300 mL of water to the precipitate obtained by decantation, thoroughly agitating, and then centrifuging and collecting the supernatant were repeated 3 times. The collected supernatant was filtered with a glass filter and vacuum concentrated to 500 mL. 2 L of denatured alcohol (2-propanol denatured ethanol, ethanol containing 1% 2-propanol) was poured into the resulting concentrated solution, and the resulting precipitate was centrifuged for 20 minutes at 8,000 rpm, and collected by removing the supernatant by decantation. The resulting precipitate was dissolved in water, and poured into methanol-denatured ethanol. These operations were repeated 3 times. The resulting precipitate was collected to obtain 3.1 g of a crude glycopeptide.

Using 25 g of Licroprep RP-8 (manufactured by Merck) as a chemically bonded silica gel resin, the resin was washed with methanol and substituted with water. 1.5 g of the crude glycopeptide dissolved in 20 mL of water was added to the water-substituted resin. Elution to the resin with the crude glycopeptide added thereto with water was performed. The eluate following salt was freeze-dried to obtain 80 mg of a glycopeptide.

Figure 7:
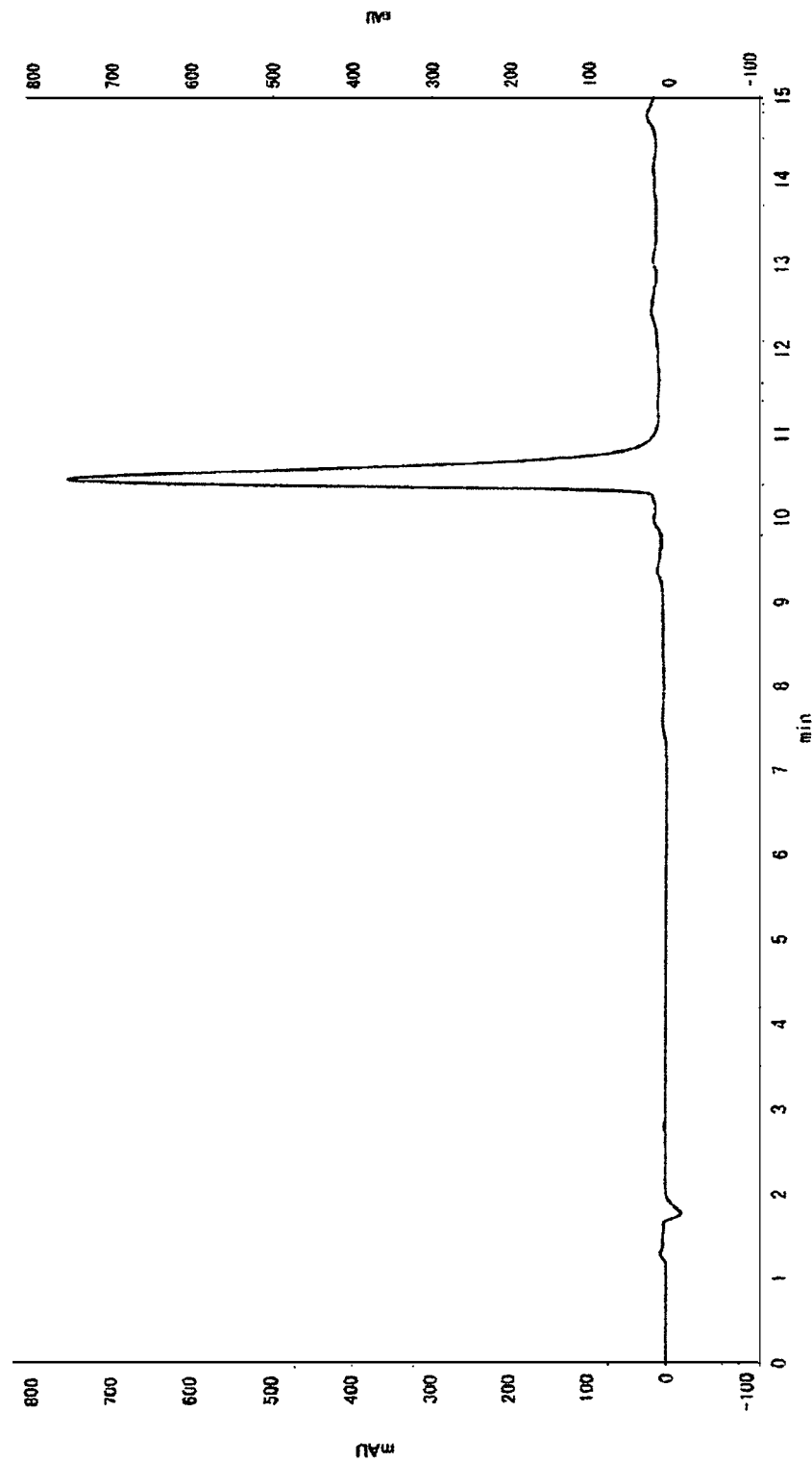
FIG. 7 shows a HPLC chart of an 11-sugar sialylglycopeptide manufactured in Example 6.

The result of HPLC measurement of the resulting glycopeptide is shown in FIG. 7. The purity was 94% according to HPLC. The resulting glycopeptide was shown by comparison with a Tokyo Chemical Industry standard product to have the structure represented by Formula 1 described above.

Example 7

1 L of water was added to 400 g of defatted egg yolk powder (manufactured by Kewpie), and thoroughly agitated. The resulting mixture was centrifuged for 20 minutes at 6,500 rpm, and a supernatant was obtained by decantation. The operations of adding 400 mL of water to the precipitate obtained by decantation, thoroughly agitating, and then centrifuging and collecting the supernatant were repeated 3 times. All the collected supernatant was filtered with a glass filter (manufactured by Whatman, GF/B) and vacuum concentrated to 500 mL. The resulting concentrated solution was poured into 2.5 L of ethanol, and the resulting precipitate was collected by 20 minutes of centrifugation at 6,500 rpm. The resulting precipitate was dissolved in 500 mL of water, and poured into 2.5 L of ethanol. These operations were repeated 3 times. The resulting final precipitate was collected to obtain 3.2 g of crude glycopeptide.

Using 150 g of Wakogel (100C18) silica gel resin as the ODS resin, the resin was washed with methanol and substituted with water. 3.2 g of the crude glycopeptide dissolved in 100 mL of water was added to the water-substituted resin. The resin with the coarsely purified glycopeptide added thereto was washed with 400 mL of water, and the glycopeptide was eluted with 2% aqueous acetonitrile solution. The eluate was freeze-dried to obtain 424 mg of a glycopeptide.

Figure 8:
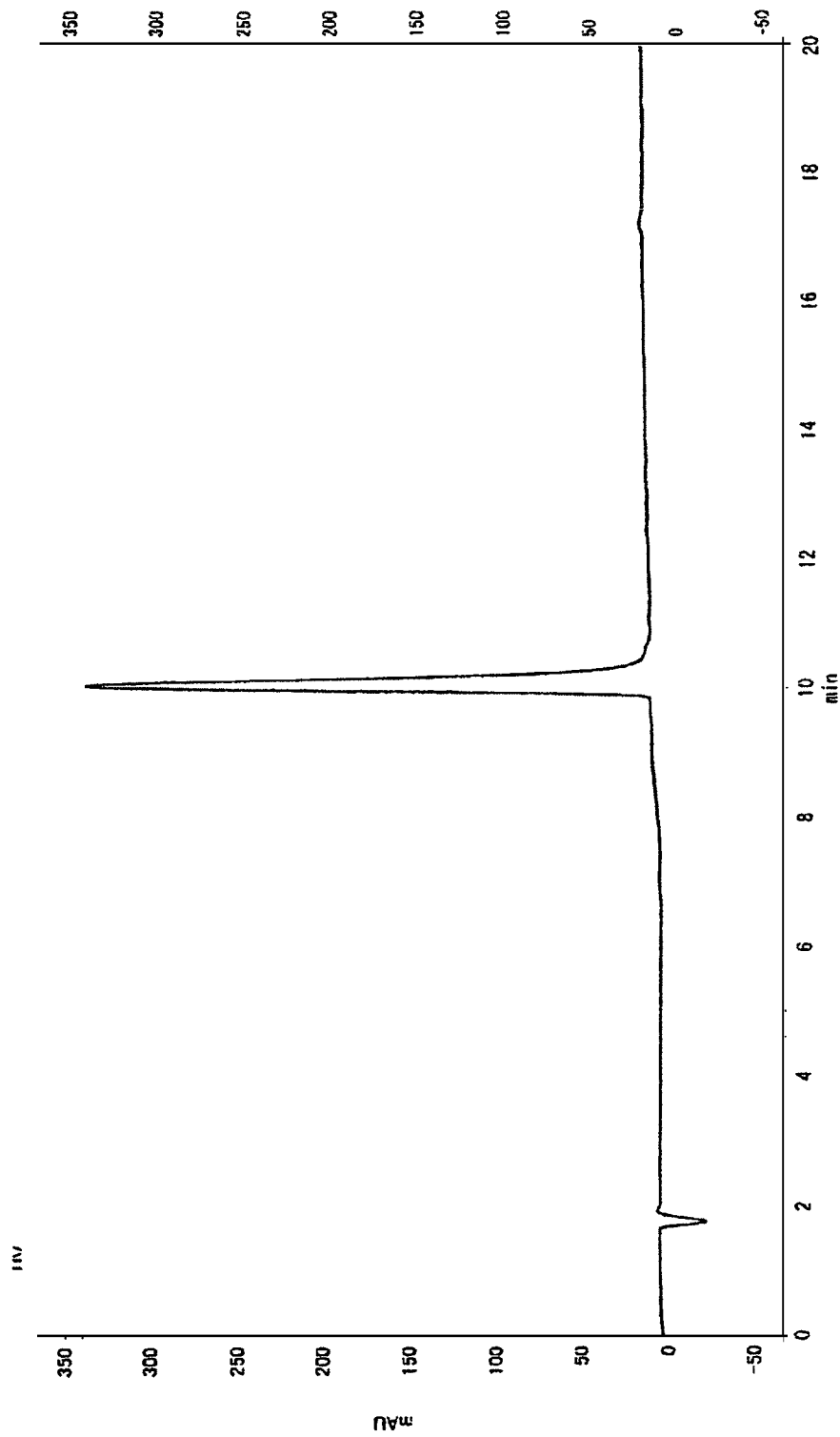
FIG. 8 shows a HPLC chart of an 11-sugar sialylglycopeptide manufactured in Example 7.

The result of HPLC measurement of the resulting glycopeptide is shown in FIG. 8. The purity was 96% according to HPLC. Using a GL Sciences HPLC GL-7400 System with a Cadenza CD-C18 column (Imtakt, 150×2 mm), HPLC analysis was performed under the following conditions: Gradient: 2%→17% (15 min)→90% (20 min), $CH_3CN$ in 0.1% TFA solution; Flow rate: 0.3 mL/min; detection UV: 214 nm. The resulting glycopeptide was shown by comparison with a standard product (manufactured by Tokyo Chemical Industry) to have the structure represented by Formula 1 described above.

Example 8

350 mL of ethanol was added to 10 chicken egg yolks, and thoroughly agitated. The resulting mixture was centrifuged for 20 minutes at 8,000 rpm, and the supernatant was removed by decantation to obtain a precipitate. The operations of adding 300 mL of ethanol to the resulting precipitate, thoroughly agitating, and then centrifuging and removing the supernatant were repeated 3 times to obtain 160 g of defatted egg yolks as a precipitate.

cipitate was dissolved in 100 mL of water, and then poured again into 700 mL of ethanol. These operations were repeated 3 times. The resulting precipitate was collected to obtain 1.7 g of crude glycopeptide.

Using 50 g of Wakogel (100C18) silica gel resin as the ODS resin, the resin was washed with methanol and substituted with water. 1.7 g of the crude glycopeptide dissolved in 10 mL of water was added to the water-substituted resin. The resin with the coarsely purified glycopeptide added thereto was washed with 100 mL of water, and the glycopeptide was eluted with 4% aqueous acetonitrile solution. The eluate was freeze-dried to obtain 120 mg of a glycopeptide.

Figure 9:
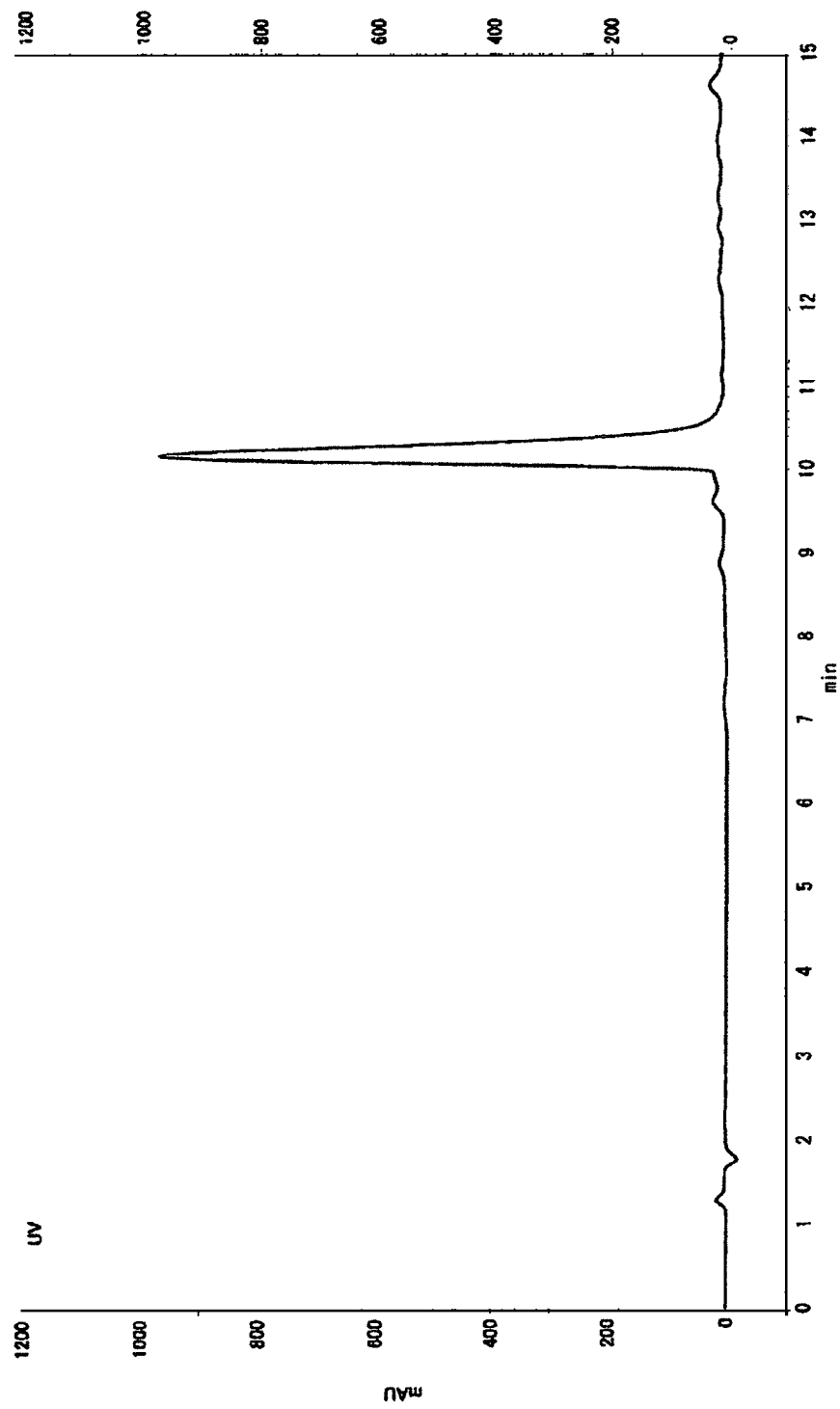
FIG. 9 shows a HPLC chart of an 11-sugar sialylglycopeptide manufactured in Example 8.

The result of HPLC measurement of the resulting glycopeptide is shown in FIG. 9. In HPLC analysis, the purity of the peak matching the elution time of a standard product (manufactured by Tokyo Chemical Industry) was 91%.

(Cross-Reference to Related Applications)

The present application is based on Japanese Patent Application 2009-203340 submitted on Sep. 3, 2009 and Japanese Patent Application No. 2010-005002 submitted on Jan. 13, 2010, and the contents thereof are incorporated herein by reference.

Industrial Applicability

The present invention can provide a production method of an 11-sugar sialyiglycopeptide from defatted bird egg yolks easily, with good yield and a high degree of purity on an industrial scale.

Seq. ID No. 1 represents the peptide sequence Lys-Val-Ala-Asn-Lys-Thr in which the sialyloligosaccharide is bound to the Asn residue.

[Sequence Table]

```
SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: sialylglycopeptide represented by formula 1
<220> FEATURE:
<221> NAME/KEY: CARBOHYD
<222> LOCATION: (4)..(4)
<223> OTHER INFORMATION: Asn glycosylated by sialooligosaccharide chain

<400> SEQUENCE: 1

Lys Val Ala Asn Lys Thr
1               5
```

200 mL of water was added to 160 g of the resulting defatted egg yolks described above, and thoroughly agitated. The resulting mixture was centrifuged for 20 minutes at 8,000 rpm, and a supernatant was obtained by decantation. The operations of adding 100 mL of water to the precipitate obtained by decantation, thoroughly agitating, and then centrifuging and collecting the supernatant were repeated 3 times. The collected supernatant was filtered with a glass filter (manufactured by Whatman, GF/B), and vacuum concentrated to 150 mL. The resulting concentrated solution was poured into 750 mL of ethanol, and the resulting precipitate was centrifuged for 20 minutes at 8,000 rpm, and collected by removing the supernatant by decantation. The resulting pre-

We claim:

1. A production method of an 11-sugar sialylglycopeptide, comprising:
    an extraction step of extracting defatted bird egg yolks with water or a salt solution to obtain a liquid extract of a glycopeptide,
    a precipitation step of adding the liquid extract to a water-soluble organic solvent to precipitate the glycopeptide, wherein the water-soluble organic solvent is selected from the group consisting of ethanol, ethanol containing 1% methanol, and ethanol containing 1% 2- propanol, and
    a desalting step of desalting the precipitate.

2. The production method according to claim 1, wherein the desalting step is a step in which the precipitate is retained on a resin and then washed with water.

3. The production method according to claim 2, wherein the resin is a reverse-phase partition chromatography resin.

4. The production method according to claim 3, wherein the reverse-phase partition chromatography resin is a chemically bonded silica gel resin.

5. The production method according to claim 4, wherein the chemically bonded silica gel resin is a resin composed of silica chemically bonded with a group selected from the group consisting of dimethyloctadecyl, octadecyl, dimethyloctyl, octyl, butyl, ethyl, methyl, phenyl, cyanopropyl and aminopropyl groups.

6. The production method according to claim 2, wherein the desalting step further comprises a step of eluting the 11-sugar sialylglycopeptide with an aqueous organic solvent.

7. The production method according to claim 6, wherein the aqueous organic solvent contains at least one selected from the group consisting of acetonitrile, methanol and ethanol.

8. The production method according to claim 6, wherein the concentration of the aqueous organic solvent is from 0.1 to 20% (v/v).

9. The production method according to claim 1, wherein the 11-sugar sialylglycopeptide is a glycopeptide represented by the following Formula 1.

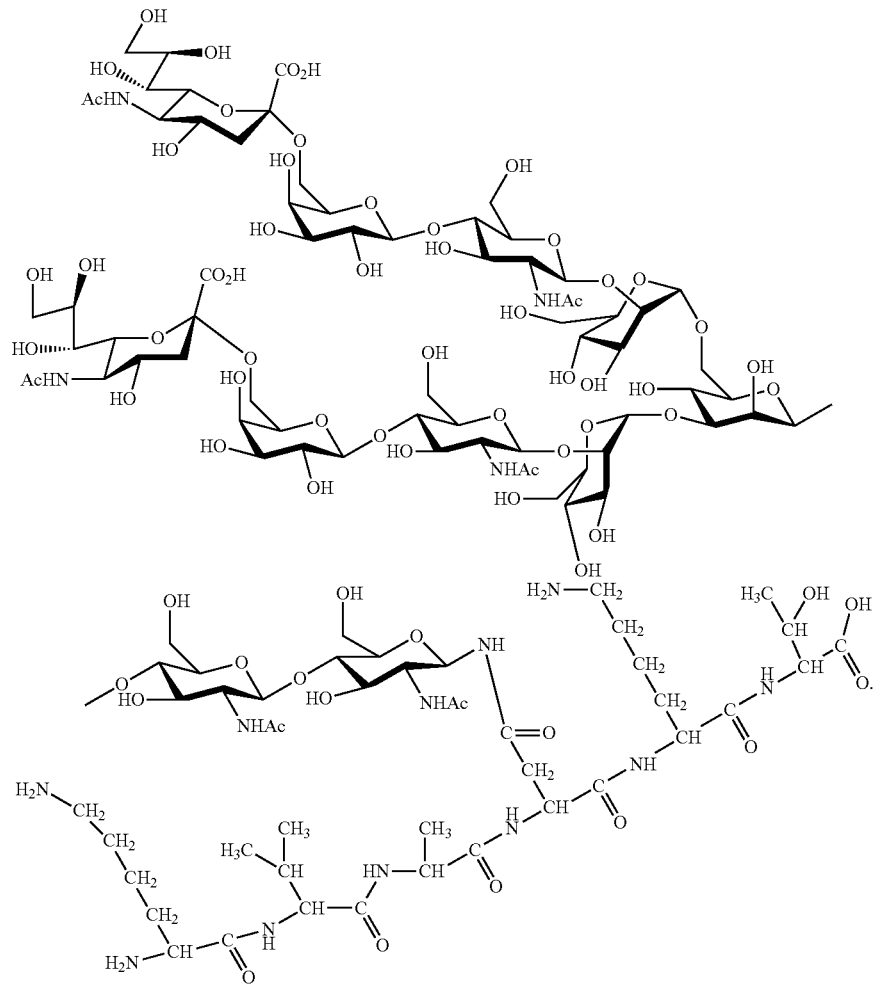

10. The production method according to claim 1, wherein the water-soluble organic solvent is ethanol.

11. The production method according to claim 1, wherein the water-soluble organic solvent is ethanol containing 1% methanol.

12. The production method according to claim 1, wherein the water-soluble organic solvent is ethanol containing 1% 2-propanol.

13. A production method of an 11-sugar sialylglycopeptide, comprising:
    an extraction step of extracting defatted bird egg yolks with water to obtain a liquid extract of a glycopeptide,
    a precipitation step of adding the liquid extract to ethanol to precipitate the glycopeptide, and
    a desalting step of desalting the precipitate with an octadecyl silica gel resin (ODS resin).

14. The production method according to claim 13, wherein the 11-sugar sialylglycopeptide is a glycopeptide represented by the following Formula 1.

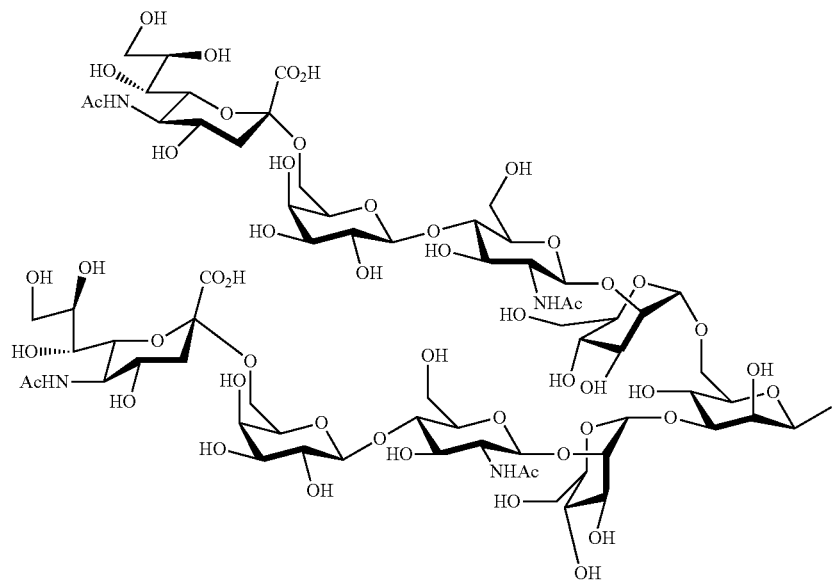

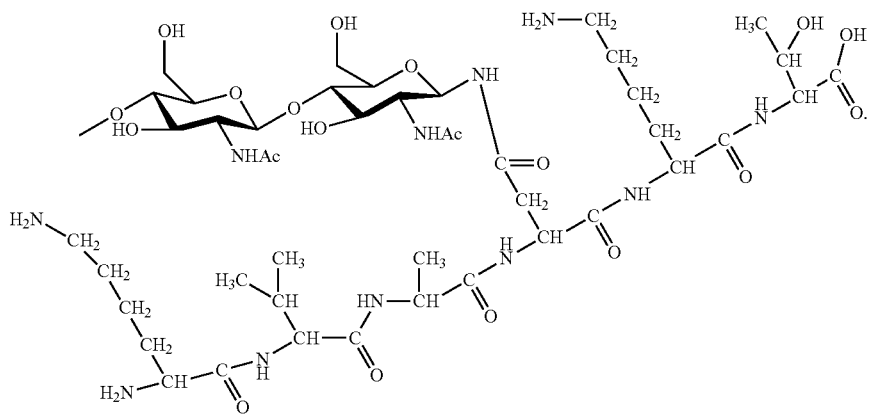

15. A production method of an 11-sugar sialylglycopeptide, comprising:
   an extraction step of extracting defatted bird egg yolks with water to obtain a liquid extract of a glycopeptide,
   a precipitation step of adding the liquid extract to ethanol to precipitate the glycopeptide, and
   a step of retaining the precipitate on an octadecyl silica gel resin (ODS resin), washing the precipitate on the ODS resin with water, and then eluting the glycopeptide with an aqueous organic solvent.

16. The production method according to claim 15, wherein the 11-sugar sialylglycopeptide is a glycopeptide represented by the following Formula 1.

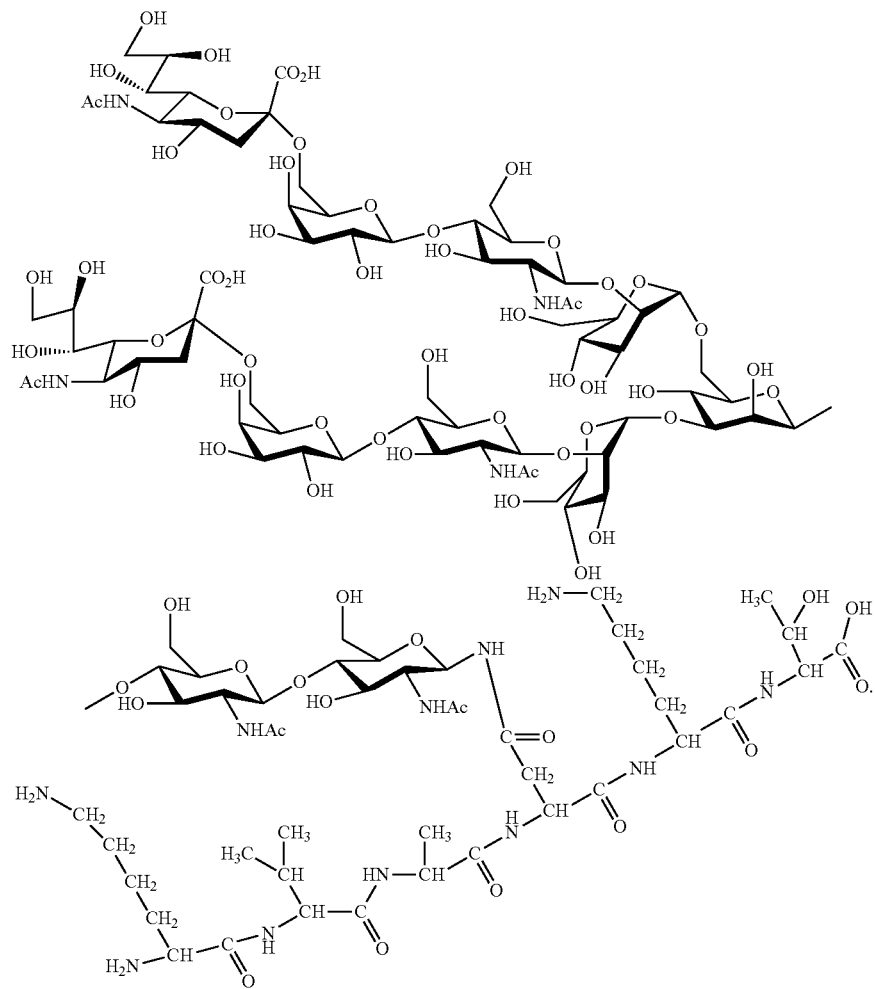
* * * * *